United States Patent [19]

Curtis

[11] Patent Number: 4,485,037
[45] Date of Patent: Nov. 27, 1984

[54] NAIL POLISH REMOVER

[75] Inventor: Ernest S. Curtis, Naugatuck, Conn.

[73] Assignee: Chesebrough-Pond's Inc., Greenwich, Conn.

[21] Appl. No.: 519,649

[22] Filed: Aug. 2, 1983

[51] Int. Cl.$^3$ .................. C11D 1/94; A61K 7/047
[52] U.S. Cl. ................... 252/546; 252/364; 252/153; 252/547; 424/61; 134/38
[58] Field of Search ............ 252/364, 546, 153; 424/61; 134/38

[56] References Cited

U.S. PATENT DOCUMENTS

| 3,907,580 | 9/1975 | van Ham | 424/61 |
| 4,032,464 | 6/1977 | Mausner | 424/61 |
| 4,110,263 | 8/1978 | Lindemann et al. | 424/70 |
| 4,240,450 | 12/1980 | Grollier et al. | 424/72 |
| 4,381,294 | 4/1983 | Bouillon et al. | 424/61 |

*Primary Examiner*—Richard D. Lovering
*Assistant Examiner*—Anne Brookes
*Attorney, Agent, or Firm*—Millen & White

[57] ABSTRACT

The fingernail water removal activity of aqueous acetone based polish removers is lowered by incorporating therein an amine salt of an anionic amidized hydrolyzed collagen, preferably in combination with an acid addition salt of amidized trialkylamine cationic surfactant.

9 Claims, No Drawings

NAIL POLISH REMOVER

BACKGROUND OF THE INVENTION

This invention relates to an improved aqueous acetone-based nail polish remover.

Nail polish is readily removed with pure acetone. However, acetone alone has a severe dehydrating effect upon skin, finger and toe nails, which is irritating to the former and renders the latter susceptible to cracking and breaking. Therefore, acetone-based commercial nail polish removers all contain other ingredients, e.g., water and/or oils, which lower this dehydrating effect but with the inevitable consequence that the efficacy of the polish remover is lowered. For example, Cutex ®, a well known acetone-based polish remover, has about 53% of the polish removal efficacy of pure acetone. Several other commercial brands, e.g., Quickie Instant ®, Unpolish ® and Dip It ®, have substantially less.

It would be desirable if the nail water removal activity of aqueous acetone based polish removers which have high polish removal efficacy, e.g., those containing at least about 80% acetone and which have at least half the water removal activity of pure acetone, could be substantially lowered without adversely affecting their polish removal efficacy. To date, no such polish remover formulation is known to exist.

It is an object of this invention to provide an aqueous acetone-based nail polish remover having high polish remover efficacy but less nail water removal activity than corresponding conventional polish removers. It is another object to provide a method of removing nail polish employing the novel polish removers of this invention. Other objects will be apparent to those skilled in the art to which the invention pertains.

SUMMARY OF THE INVENTION

In a composition aspect, this invention relates to aqueous acetone-based nail polish removers comprising, in solution therein an amount of water soluble amine salt of a fatty acid amide of a hydrolyzed collagen, effective to reduce substantially the nail water removal activity of the polish remover.

In a method of use aspect, this invention relates to a method of removing nail polish employing a polish remover of this invention.

DETAILED DISCUSSION

In the discussion and Examples hereinafter, all percentages are by weight.

The polish removers of this invention are acetone based, i.e., they consist of at least about 80%, preferably at least 85% and most preferably about 87% (±1.0%) of acetone. They are aqueous, i.e., they contain about 5% to 20%, preferably about 10% to 15%, and most preferably about 12% (±0.5%). The aqueous acetone ordinarily constitutes at least about 90%, usually at least 95% and most preferably about 99% ( 1%) of the remover.

The polish removers of this invention are characterized by the presence in solution therein of an amount of an amidized hydrolyzed collagen derivative which renders the hydrolyzed collagen, anionic, preferably 0.01% to 0.15%, more preferably 0.03% to 0.04%.

Hydrolyzed collagen is, of course, a well known conventional commercial product suitable for many uses, including gels which form colloidal aqueous solutions. The hydrolyzed collagen employed in this invention has been amidized, i.e., at least the terminal free amino group has been converted to a carboxylic acid amide group in a conventional manner.

These amidized hydrolyzed collagen can be represented substantially by the formula

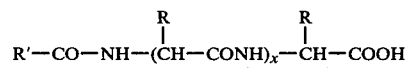

wherein R is the side chain of a primary or α-amino acid polymer unit of the hydrolyzed collagen, e.g., CH$_3$— for alanine, CH$_3$CHOH— for threonine, p-hydroxybenzyl for tyrosine, x is an integer from about 20 to 40, and R'—CO— is the acyl radical of the amidizing acid, which preferably is a fatty acid, more preferably of 5 to 18 carbon atoms, e.g., undecylic, lauric, myristic, palmitic, margaric, stearic, isostearic, nonadecylic, and the corresponding unsaturated acids, e.g., sorbic and linoleic.

The conversion of accessible primary amine groups of hydrolyzed collagen to amide groups, imparts an anionic charge to the hydrolyzed protein, which permits it to form stable salts with bases, such as organic amines, e.g., alkyl and hydroxyalkyl amines of 1-4 carbon atoms, in the alkyl group, e.g., dialkyl and alkylamines, preferably those wherein each alkyl is of 1-4 carbon atoms, e.g., trimethylamine and diethylamine, alkanolamines, preferably wherein the alkanol is of 1-4 carbon atoms, e.g., ethanolamine, propanolamine and aminomethylpropanol, etc. The exact nature of the amine which forms the salt is not critical, as long as the salt formed therewith is cosmetically acceptable and is soluble in aqueous acetone.

An especially preferred salt of a fatty acid amide of hydrolyzed collagen (b) is the aminomethylpropanol salt of isostearic amide of hydrolyzed collagen, available from Croda, Inc., 51 Madison Avenue, New York, N. Y. 10010, under the trademark "Crotein AD Anhydrous" as a light to medium yellow clear liquid having a solids content (after drying for 2 hours at 110° C.) of 32.0–36.0%, a pH (as a 10% aqueous solution at 25° C.) of 8.0–9.0, a specific gravity (at 25° C.) of 0.830–0.850, and an acid value of 40–55.

The preferred polish removers of this invention contain a cationic surfactant, viz., an acid addition salt of an amidoamine, as well as an amine salt of a water soluble amido hydrolyzed collagen. Collagen hydrolyzates have a demonstrable conditioning and protective effect on hair, skin and nails. Its presence in an aqueous acetone based polish remover reduce substantially its water removing activity. However, the amount thereof required to achieve a substantial reduction is such activity, viz., to about a third or less of pure acetone, in about twice that required when used in combination with a cationic surfactant of this invention. Moreover, the combination imparts a superior water loss resisting film on the nails than either ingredient alone.

The preferred polish removers of this invention are characterized by comprising an amount of a cosmetically acceptable acid addition salt of a mono-fatty acid-amide substituted-trialkylamine cationic surfactant effective to further reduce the nail water removal activity of the polish remover, e.g., from 0.10% to 0.80%, preferably 0.20% to 0.25%.

The preferred amido-substituted trialkylamine salts are those of the formula R—CO—NH—alkylene—N-(alkyl)$_2$.R'COOH wherein R—CO— is the acyl radical of a lipophylic acid, e.g., a fatty acid, preferably of 5 to 18 carbon atoms, e.g., as exemplified hereinbefore for the amidized hydrolyzed collagen; alkylene is the alkyl group bearing the amide substituent, viz., a bridging divalent alkylene group, preferably of 2-6 carbon atoms, e.g., ethylene, propylene, isopropylene, butylene, butylene-1,3 and butylene-2,4; alkyl is preferably lower alkyl of 1-6 carbon atoms, e.g., CH$_3$, C$_2$H$_5$ and isoC$_3$H$_7$; and R'COOH is the acid forming the acid addition salt with the amine, e.g., a lower fatty acid, e.g., of 1-6 carbon atoms, such as acetic, propionic, butyric, valeric, or a corresponding acid bearing one or more substituents, e.g., hydroxy, and/or additional carboxy groups. The exact chemical nature of the acid is not critical, the only requirement being that the salt formed therefrom is soluble in the aqueous acetone employed and is cosmetically acceptable. The preferred amines are those wherein alkyl is methyl or ethyl, wherein alkylene is —(CH$_2$)$_3$—, or wherein R—CONH— is cocoamido.

An especially preferred amine salt (a) is cocoamidopropyl,-dimethylamine propionate, a compound of the formula

RCONH—(CH$_2$)$_3$—N(CH$_3$)$_2$.CH$_3$CH$_2$CO$_2$H wherein R represents the mixture of aliphatic hydrocarbon groups provided by the mixture of amines present in cocoamine, e.g., R is a mixture of hydrocarbon aliphatic groups of from 8 to 18 carbon atoms, including both straight and branched chain and saturated and unsaturated. This salt is commercially available from The Richardson Co., 100 New Street, Patterson, N.J. 07501 under the trademark "EMCOL 1655."

As would be obvious to one skilled in the art, the amine salt (a) and hydrolyzed collagen derivative (b) of this invention must be cosmetically, i.e., dermatologically acceptable, i.e., they must be essentially odorless, colorless and storage stable in aqueous acetone and they must be free of allergenic or toxic effects in the amounts employed when removing nail polish.

As is also obvious because (a) is a salt of a cationic amine and (b) is a salt of an anionic collagen derivative, salt exchange can occur between (a) and (b) so that in solution, the amidized hydrolyzed collagen anion of (b) and the amido substituted tertiary amine cation of (a) may exist as a cationic-anionic complex, which may be responsible for the synergistic effect of the combination of (a) and (b) in lowering nail water loss activity of the polish remover. Therefore, the phrase "comprises as ingredients thereof" as used herein embraces (a) and (b) in such cationic-anionic complex form.

Optional ingredients in the polish removers of this invention are the conventional cosmetic excipients, such as coloring agents, perfumes, viscosity raising agents, emollients, etc. A moisture impermeable film former, e.g., nitrocelluose, can also be present to further inhibit moisture loss from the nails.

Contemplated equivalents of the fatty acid amide hydrolyzed collagen derivatives employed in this invention are other film forming derivatives of hydrolyzed collagen which impart comparable anionic charge to the hydrolyzed collagen which enables it to form salts with weak cations, such as amines. Contemplated equivalents of the amido substituted trialkyl amine surfactants are other tertiary amine surfactants bearing a lipophilic group and having a cationic charge which enables it to form water soluble salts with weak acids, such as fatty acids. As will be apparent to those skilled in the art, when both the anionic hydrolyzed collagen derivative and the cationic surfactant are present in a polish remover of this invention, they can be employed as an acetone solution of their non-salt form, thereby forming a salt of each other in the polish remover.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLES

The following are examples of nail polish removers of this invention:

|  | I | II | III | IV | V |
|---|---|---|---|---|---|
| Acetone | 87.1% | 87% | 86.9% | 87.4% | 87.5% |
| Water (deionized) | 12% | 12% | 11.9% | 12.1% | 12.1% |
| Cocamidopropyl dimethylamine propionate (a) (EMCOL 1655) | 0.5% | 0.5% | 0.5% | — | — |
| Aminomethylpropanol salt of isostearic hydrolyzed collagen (b) (Crotein AD Anhydrous | 0.1% | 0.1% | 0.1% | 0.2% | 0.1% |
| Fragrance | 0.2% | 0.3% | 0.2% | 0.2% | 0.2% |
| Color (D & C Yellow #11 in Acetone) | 0.1% | 0.1% | 0.1% | 0.1% | 0.1% |
| Green | — | — | 0.3% | — | — |

Each of the foregoing has about the same polish removal efficacy, i.e., about 53% of pure acetone, as the corresponding formulations lacking both (a) the amidoamine salt and (b) the hydrolyzed collagen derivative, but only about 34% of the fingernail water removal activity thereof. The formulations of Examples IV and V, which contain only (b) of Examples I-III, have the same polish removal efficacy and about 39% and 48%, respectively, of the water removal activity of the corresponding formulation lacking both (a) and (b). A formulation corresponding to Examples I-III but lacking (b) has about 54% of the water removal activity thereof.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an aqueous acetone-based nail polish remover containing at least about 80% acetone, the improvement wherein the remover comprises in solution (a) from 0.01% to 0.15% of a cosmetically acceptable water soluble amine salt of a fatty acid amide of a hydrolyzed collagen of the formula

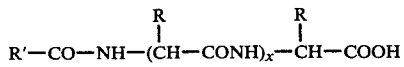

wherein R is the side chain of a primary or α-amino acid polymer unit of the hydrolyzed collagen, x is an integer from about 20 to 40, and R'—CO— is an acyl radical of the amidizing fatty acid of from 5 to 18 carbon atoms, and (b) from 0.1% to 0.8% of a cosmetically acceptable acid addition salt of a mono-fatty acid-amido substituted-trialkylamine cationic surfactant, in amounts effective to reduce substantially the nail water removal activity of the acetone of the polish remover.

2. A polish remover formulation according to claim 1 containing about 0.03% to 0.04% of the water soluble amine salt.

3. A polish remover formulation according to claim 1 wherein the amide group is isostearicamido.

4. A polish remover formulation according to claim 1 wherein the amine salt is the aminomethylpropanol salt.

5. A polish remover formulation according to claim 1 wherein the amine salt is the aminomethylpropanol salt of isostearicamido-hydrolyzed collagen.

6. A polish remover formulation according to claim 2 wherein the amine of the surfactant is cocoamido-tri-lower-alkyl-amine.

7. A polish remover formulation according to claim 6 wherein the surfactant is cocoamidopropyl, dimethylamine propionate.

8. A polish remover formulation according to claim 1 consisting essentially of an aqueous acetone solution of (a) the aminomethylpropanol salt of the isostearic amide of hydrolyzed collagen and (b) cocoamidopropyl dimethylamine propionate.

9. A polish remover formulation according to claim 8 consisting essentially of about 87% acetone; about 12% of water; about 0.1% of (a) and about 0.5% of (b).

* * * * *